United States Patent

Kanai et al.

[11] 4,142,041
[45] Feb. 27, 1979

[54] NOVEL N[4]-ACYLOXY-2,2'-CYCLOCYTIDINES AND PROCESS FOR PREPARATION THEREOF

[75] Inventors: Tadashi Kanai; Osamu Maruyama, both of Kokybunji; Akiji Aoki, Itsukaichi, all of Japan

[73] Assignee: Kohjin Co., Ltd., Tokyo, Japan

[21] Appl. No.: 828,114

[22] Filed: Aug. 26, 1977

[30] Foreign Application Priority Data

Aug. 30, 1976 [JP] Japan .................. 51-102576
Sep. 3, 1976 [JP] Japan .................. 51-104982

[51] Int. Cl.[2] ............... C07H 17/00; A61K 31/70
[52] U.S. Cl. ......................... 536/23; 424/180
[58] Field of Search ........................... 536/23

[56] References Cited
U.S. PATENT DOCUMENTS

| 399,104 | 11/1976 | Ishida et al. ............ 536/23 |
| 3,792,040 | 2/1974 | Moffatt et al. .......... 536/23 |
| 3,920,630 | 11/1975 | Wechter et al. ......... 536/23 |

Primary Examiner—Johnnie R. Brown
Assistant Examiner—Blondel Hazel
Attorney, Agent, or Firm—Sughrue, Rothwell, Mion, Zinn and Macpeak

[57] ABSTRACT

N[4]-Acyloxy-2,2'-cyclocytidines of the formula:

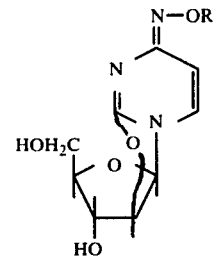

and N[4], 3',5'-tri-O-acyl-2,2'-cyclocytidines of the formula:

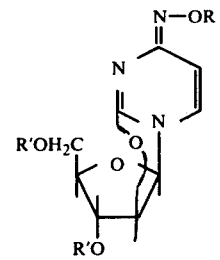

wherein R' and R are the same and represent an acyl group; which are useful for decreasing the total packed cell volume ratio (T/C%) with respect to ascitic form of Sarcoma 180 in small animals, and thus prolonging their lives.

4 Claims, No Drawings 4,142,041

NOVEL N⁴-ACYLOXY-2,2'-CYCLOCYTIDINES AND PROCESS FOR PREPARATION THEREOF

BACKGROUND OF THE INVENTION

1. FIELD OF THE INVENTION

This invention relates to novel $N^4$-acyloxy-2,2'-cyclocytidines and $N^4$,3',5'-tri-O-acyl-2,2'-cyclocytidines which decrease the total packed volume ratio (T/C%) with respect to ascitic form of Sarcoma 180 in small animals, and have an effect of prolonging their lives.

2. DESCRIPTION OF THE PRIOR ART 2,2'-Cyclocytidine is known to be useful as an antileukemic agent having few side-effects and has been clinically evaluated in many countries (e.g., as disclosed in Y. Sakai et al., *Japan J. Clin. Oncol.*, 2, 57 (1972)), and a method for treating leukemia is disclosed in German Patent (DAS) No. 2,159,181 and French Pat. No. 2,138,603 (both corresponding to U.S. patent Ser. No. 598,897, filed July 24, 1975).

A wide variety of 2,2'-cyclocytidine derivatives have also been disclosed in the art. For example, British Pat. No. 1,325,798 (corresponding to U.S. patent application Ser. No. 75,272, filed Sept. 24, 1970) discloses 2,2'-anhydro-ara-cytidine derivatives having a 5'-O-acyl group and a 4-imino salt group which are said to have antiviral, antitumour and immunosuppressive activities. Japanese Patent Application (OPI) No. 16,481/1972 (corresponding to U.S. patent application Ser. No. 110,312, filed Jan. 27, 1971) discloses a method of preparation of 3',5'-di-O-acyl-aracytidines having excellent immunosuppressive, antitumour and anti-leukemic activities by acylating 2,2'-cyclocytidine to introduce an aromatic acyl group and through 3'-O-, 5'-O- and $N^4$-triacyl-cyclocytidine as an intermediate. U.S. Pat. No. 3,709,874 discloses 1-β-D-arabino-furanosyl cytosine derivatives having antiviral and cytotoxic activities.

Some cyclocytidine derivatives, i.e., $N^4$-substituted-2,2'-cyclocytidines, have been reported to have an antileukemic activity in experimental animals approximately equivalent to or higher than that of the parent compound, 2,2'-cyclocytidine (e.g., as disclosed in Kanai, et al., *J. Med. Chem.*, Vol. 17, page 1076 (1974)). Typical examples of such $N^4$-substituted-2,2'-cyclocytidines are $N^4$-hydroxy-2,2'-cyclocytidine, $N^4$-hydroxy-5'-acetyl-2,2'-cyclocytidine, $N^4$-O-alkyl-2,2'-cyclocytidine, etc., as disclosed in Japanese Patent Application (OPI) No. 23788/1973, in British Pat. No. 1,386,334 and in French Pat. No. 2,199,460, $N^4$-hydroxy-3'-O-benzoyl or -O-acetyl, -O-palmitoyl derivatives, etc., of 2,2'-cyclocytidine as disclosed in Japanese Patent Application (OPI) No. 88095/1975, $N^4$-hydroxy-5'-O-benzoyl or -O-acetyl, -O-adamantoyl derivatives, etc., of 2,2'-cyclocytidine as disclosed in Japanese Patent Application (OPI) No. 88097/1975, $N^4$-hydroxy-3',5'-di-O-acetyl or di-O-stearoyl, di-O-hexanoyl derivatives, etc., of 2,2'-cyclocytidine as disclosed in Japanese Patent Application (OPI) No. 88096/1975 and in British Pat. No. 1,480,120.

SUMMARY OF THE INVENTION

This invention provides a new class of $N^4$-acyloxy- and $N^4$,3',5'-tri-O-acyl-2,2'-cyclocytidines which show a decreased total packed cell volume ratio (T/C%) with respect to ascitic form of Sarcoma 180 in small animals and exhibit an effect of prolonging their lives.

More specifically, the invention provides cyclocytidine derivatives of the following formula (I):

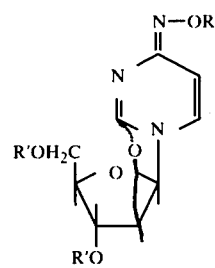

wherein the two R' moieties both represent a hydrogen atom, or are the same as R which represents an acyl group derived from a fatty acid containing 1 to 46 carbon atoms or a cyclic carboxylic acid containing 5 to 11 carbon atoms with the ring being optionally substituted with one or more of a chlorine atom, a methyl group, a methoxy group, or a nitro group.

DETAILED DESCRIPTION OF THE INVENTION

The $N^4$-acyloxy-2,2'-cyclocytidines of the general formula (I):

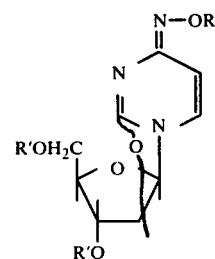

wherein the two R' moieties both represent a hydrogen atom, or are the same as R which represents an acyl group derived from a fatty acid containing 1 to 46 carbon atoms or a cyclic carboxylic acid containing 5 to 11 carbon atoms with the ring being optionally substituted with one or more of a chlorine atom, a methyl group, a methoxy group or a nitro group; and the pharmaceutically acceptable salts thereof, and $N^4$,3',5'-tri-O-acyl-2,2'-cyclocytidines (compounds of the formula (I) in which the two R' moieties are the same as R) and the pharmaceutically acceptable salts thereof are prepared by reacting $N^4$-hydroxy-2,2'-cyclocytidine (as disclosed in Kanai, et al., *J. Med. Chem.*, Vol. 17, page 1076 (1974)) of the formula (II):

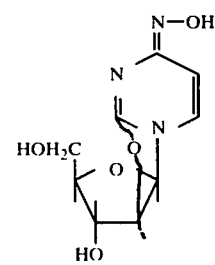

or the salts thereof either with an acylating agent which is an acid halide, an acid anhydride or a mixed acid anhydride of fatty acids containing 1 to 46 carbon atoms or a cyclic carboxylic acid containing 5 to 11 carbon atoms with the cyclic ring being optionally substituted with one or more of a chlorine atom, a methyl group, a methoxy group or a nitro group or with the said acids in the presence of a condensing agent. More specifically, the $N^4$-acyloxy-2,2'-cyclocytidines and their pharmaceutically acceptable salts can be prepared by conducting the above-described reaction in a hydrophilic solvent or in a water-containing hydrophilic solvent; and the $N^4,3',5'$-tri-O-acyl-2,2'-cyclocytidines and their pharmaceutically acceptable salts can be produced by conducting the above-described reaction in the presence of an amine or an alkali metal.

A preferred class of compounds of this invention includes those of the formula (I) wherein the two R' moieties are both a hydrogen atom, or are the same as R which represents an acyl group derived from a fatty acid containing 1 to 20 carbon atoms or a cyclic carboxylic acid containing 5 to 11 carbon atoms with the cyclic ring being optionally substituted with one or more of a chlorine atom, a methyl group, a methoxy group or a nitro group; and their pharmaceutically acceptable salts.

A further preferred class of compounds includes those of the formula (I) wherein the two R' moieties are both a hydrogen atom, or are the same as R which represents an acetyl, propionyl, butyryl, valeryl, hexanoyl, heptanoyl, octanoyl, decanoyl, lauroyl, myristoyl, palmitoyl, stearoyl, benzoyl, p-chlorobenzoyl, p-nitrobenzoyl, phenylacetyl, p-toluyl, o-toluyl, 3,4,5-trimethoxybenzoyl, 1-adamantancarbonyl, 5-norbornene-2-carbonyl or cyclobutanecarbonyl group; and their pharmaceutically acceptable salts.

The most preferred class of compounds includes those of the formula (I) wherein the two R' moieties are both a hydrogen atom, or are the same as R which represents an acetyl, propionyl, butyryl, valeryl, hexanoyl, heptanoyl, octanoyl, decanoyl, lauroyl, myristoyl, palmitoyl, or stearoyl group; and their pharmaceutically acceptable salts.

Examples of specific fatty acids that can be used in this invention are saturated fatty acids such as formic acid, acetic acid, propionic acid, butyric acid, isobutyric acid, valeric acid, isovaleric acid, 2-methylbutanoic acid, pivalic acid, hexanoic acid, heptanoic acid, octanoic acid, nonanoic acid, decanoic acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, hentriacontanoic acid, dotriacontanoic acid, tetratriacontanoic acid, ceroplastic acid, hexatriacontanoic acid, n-octatriacontanoic acid, n-hexatetracontanoic acid; unsaturated fatty acids such as petroselinic acid, oleic acid, linoleic acid, linolenic acid, and 6,9,12-octadecatrienoic acid; aromatic carboxylic acids such as p-methoxybenzoic acid, benzoic acid, p-chlorobenzoic acid, p-nitrobenzoic acid, phenylacetic acid, p-methylbenzoic acid, o-methylbenzoic acid, 3,4,5-trimethoxybenzoic acid, and alicyclic carboxylic acids such as 1-adamantanecarboxylic acid, 5-norbornene-2-carboxylic acid, and cyclobutanecarboxylic acid.

In the practice of the present invention, these fatty acids or cyclic carboxylic acids are used in the presence of a condensing agent such as N,N'-dicyclohexylcarbodiimide, N,N'-diethylcarbodiimide, N,N'-carbonyldi(2-methylimidazole), pentamethyleneketene-N-cyclohexylimine, diphenylketene-N-cyclohexylimine, alkoxyacetylenes (in which the alkoxy moiety has 1 to 4 carbon atoms such as methoxy, ethoxy, etc.), 1-alkoxy-1-chloroethylenes (in which the alkoxy moiety has 1 to 4 carbon atoms such as methoxy, ethoxy, butoxy, etc.), tetraalkyl phosphites (in which the alkyl moiety has 1 to 4 carbon atoms such as methyl, ethyl, etc.), isopropyl polyphosphate, phosphorus oxychloride, phosphorus trichloride, thionyl chloride, oxalyl chloride, and triphenyl phosphines. Alternatively, the acid halides, acid anhydrides or mixed acid anhydrides of these fatty acids or cyclic carboxylic acids can be used.

Examples of suitable solvents that can be used in this invention are hydrophilic solvents (i.e., those soluble in water or compatible with water) such as dioxane, acetone, acetonitrile, N,N'-dimethylformamide (DMF), N,N-dimethylacetamide (DMAC), tetramethylurea (TMU), dimethyl sulfoxide (DMSO), hexamethyl phosphoramide (HMPA), tetramethylene sulfone (sulfolane), propylene carbonate, nitromethane, dimethyl cyanamide, formic acid, acetic acid, pyridine, methanol, and ethanol.

Acylation of the $N^4$-hydroxy-2,2'-cyclocytidine in this invention can be performed using two methods, a method which comprises selectively acylating the hydroxyl group at the $N^4$-position (Method I), and a method which involves forming an $N^4,3',5'$-O-triacyl compound in a good yield (Method II). The details of these methods are described below.

METHOD I

Selective acylation of the hydroxyl group at the $N^4$-position

To increase the selectivity of acylation for the $N^4$-position hydroxyl group, the use of a hydrophilic solvent in admixture with water (e.g., preferably in an amount of about 1:3 to about 1:5 by volume of water to solvent) provides better results.

For some types of reactive derivatives of the organic carboxylic acids used, the reaction mixture is neutralized, e.g., to a pH of about 6 to 8, with a base such as an alkali metal hydrogen carbonate (for example, NaHCO$_3$, KHCO$_3$, etc.), a trialkylamine (for example, trimethylamine, triethylamine, etc.) or pyridine. Usually, however, the free organic carboxylic acid, hydrohalic acid (i.e., produced from the reaction of the acid halide with a condensing agent), etc., can be removed by washing the reaction mixture with a solvent in which the final product is scarcely soluble, such as an ether (such as, diethyl ether, dipropyl ether, etc.), acetone, methyl ethyl ketone, or an ester (such as ethyl acetate, etc.). The reaction temperature is not particularly limited, and usually ranges from about 0° C. to the reflux temperature of the reaction system. The reaction product can be separated from the reaction mixture using conventional techniques, e.g., by crystallization or extraction.

Of the acylating methods listed above, the reaction of a symmetrical acid anhydride in a water-containing hydrophilic organic solvent is particularly simple and convenient for acylating the hydroxyl group at the $N^4$-position selectively in good yields. The fatty acid anhydride is used in an amount of at least about 1 mol, preferably 2 to 3 mols, per mol of the $N^4$-hydroxy-2,2'-cyclocytidine, and water is employed in an amount of at least about 1 mol, preferably in a large excess of, for example, 20 to 150 mols, per mol of the fatty acid anhydride. The solvent is generally used in an amount of about 5 to about 100 times by weight based on the weight of the starting material $N^4$-hydroxy-2,2'-cyclocytidine. At this time, water serves to prevent the acylation of the hydroxyl group of the sugar moiety. In other words, after the acylation of the hydroxyl group at the $N^4$-position, the excess of the acid anhydride is deactivated by reaction with water.

When the reaction is performed in a solvent which does not contain water, the reaction temperature should be from about 0° C. to 100° C., preferably from 0° C. to 40° C., for the selective acylation of the $N^4$-position hydroxyl group.

The above reaction is carried out usually for about 2 to about 48 hours, but the reaction time can be changed as needed depending on the reaction temperature.

METHOD II
$N^4,3',5'$-tri-O-acylation

In order to perform the $N^4,3',5'$-tri-O-acylation in a good yield, the reaction must be performed in the presence of an amine such as pyridine, dimethylamine or diethylamine, or an alkaline earth metal carbonate such as barium carbonate or calcium carbonate. It is also necessary for the solvent to be anhydrous. In the acylation, the acylating agent is used in an amount of about 3.0 to about 15.0 mols, preferably 4 to 8 mols, per mol of the starting material. The reaction temperature is relatively high, and ranges from about 0° to about 180° C., preferably from 60° to 150° C. The reaction time is, for example, about 5 to about 40 hours. Generally, longer periods of reaction time are sometimes required as the molecular weight of the carboxylic acid increases.

In separating the final product from the reaction mixture, usually the reaction solvent is removed, and the residue is washed with a solvent in which the final product is scarcely soluble, such as diethyl ether, petroleum ether, n-hexane or methyl ethyl ketone, thereby to remove the free organic acid, etc. It is also possible to separate the product directly from the reaction mixture, e.g., by crystallization or extraction.

The $N^4$-acyloxy-2,2'-cyclocytidines and $N^4,3',5'$-tri-O-acyl-2,2'-cyclocytidines are all novel compounds, and are derivatives of 2,2'-cyclocytidine which is now used as a therapeutic agent for treating leukemia, or of $N^4$-hydroxy-2,2'-cyclocytidine whose effect is in L 1210 mouse leukemias equal to or greater than the 2,2'-cyclocytidine. It is recognized that compounds of this invention have a greater effect against certain kinds of experimental tumors than that of the parent compounds, 2,2'-cyclocytidine and $N^4$-hydroxy-2,2'-cyclocytidine, and are expected to have utility as therapeutic agents for treating cancer.

While not desiring to be bound, it is believed that the $N^4$-acyloxy-2,2'-cyclocytidines and $N^4,3',5'$-tri-O-acyl-2,2'-cyclocytidines in accordance with this invention impart an enhanced lipid affinity to the molecules thereof, thereby concentration in the lipid is increased, prevent dehydroxylation by dehydroxylase in the living body, and inhibit a change of $N^4$-hydroxy-2,2'-cyclocytidine to 2,2'-cyclocytidine and then to 1-$\beta$-D-arabinofuranosyl cytosine within the living body, thereby retaining the inherent anticancer action of $N^4$-hydroxy-2,2'-cyclocytidine for prolonged periods of time.

The $N^4$-acyloxy-2,2'-cyclocytidines and $N^4,3',5'$-tri-O-acyl-2,2'-cyclocytidines are usually obtained in the free form, although they can be produced not only in the free form but also as the pharmaceutically acceptable salts thereof such as organic acid salts or inorganic acid salts, and they can be converted into one form or the other in a conventional manner.

Suitable pharmaceutically acceptable salts include salts of organic acids such as those of formic acid, acetic acid, maleic acid, fumaric acid, succinic acid, oxalic acid, tartaric acid, citric acid or lactic acid, or salts of inorganic acids such as those of hydrochloric acid, hydrobromic acid, hydroiodic acid, or sulfuric acid.

The $N^4$-acyloxy-2,2'-cyclocytidines and $N^4,3',5'$-tri-O-acyl-2,2'-cyclocytidines and pharmaceutically acceptable salts thereof have very strong anticancer activities. Table 1 summarizes the anticancer effects of some typical examples of these compounds. It is apparent from the results shown in Table 1 that when compared with 2,2'-cyclocytidine and $N^4$-hydroxy-2,2'-cyclocytidine as controls, the compounds in accordance with this invention show favorable results in T/C% on small animals suffering from Sarcoma 180 ascitic tumor.

For evaluation of anticancer effects, $1 \times 10^7$ tumor cells (ascitic form of Sarcoma 180) were implanted intraperitoneally in the mouse. The compound to be tested was injected once daily for 5 days, starting 24 hours after inoculation. For each compound, a group of six mice was used. The anticancer effects of the compounds were evaluated by the total packed cell volume ratio (T/C%) (as defined in Note 2 of Table 1 given hereinafter) on the seventh day.

TABLE 1
Effects Against Cancer Cells

| Compound | Dose (mg/kg/day×5) | T/C (%) | Grade of T/C |
|---|---|---|---|
| $N^4$-O-Acetyl-2,2'-cyclocytidine | 300 | 2.4 | +++ |
| $N^4$-O-Propionyl-2,2'-cyclocytidine | 250 | 0.3 | " |
| $N^4$-O-Butyryl-2,2'-cyclocytidine | 250 | 10.0 | " |
| $N^4$-O-Valeryl-2,2'-cyclocytidine | 250 | 0.0 | " |
| $N^4$-O-Hexanoyl-2,2'-cyclocytidine | 250 | 0.3 | " |
| $N^4$-O-Octanoyl-2,2'-cyclocytidine | 250 | 15.0 | ++ |
| $N^4$-O-Decanoyl-2,2'-cyclocytidine | 250 | 0.0 | +++ |
| $N^4$-O-Lauroyl-2,2'-cyclocytidine | 250 | 0.0 | " |
| $N^4$-O-Myristoyl-2,2'-cyclocytidine | 250 | 0.0 | " |
| $N^4$-O-Palmitoyl-2,2'-cyclocytidine | 250 | 0.0 | " |
| $N^4$-O-Stearoyl-2,2'-cyclocytidine | 250 | 0.0 | " |
| $N^4,3',5'$-Tri-O-acetyl-2,2'-cyclocytidine | 300 | 0 | " |
| $N^4,3',5'$-Tri-O-propionyl-2,2'-cyclocytidine | 250 | 0.3 | " |
| $N^4,3',5'$-Tri-O-butyryl-2,2'-cyclocytidine | 250 | 0.5 | " |
| $N^4,3',5'$-Tri-O-valeryl-2,2'-cyclocytidine | 250 | 0 | " |
| $N^4,3',5'$-Tri-O-hexanoyl-2,2'-cyclocytidine | 250 | 0.3 | +++ |
| $N^4,3',5'$-Tri-O-stearoyl-2,2'-cyclocytidine | 250 | 15.1 | ++ |
| $N^4$-Hydroxy-2,2'-cyclocytidine | 250 | 0.4 | +++ |
| 2,2'-Cyclocytidine | 250 | 0.8 | " |

NOTE 1

The cancer cells used in examining anticancer activities were ascitic Sarcoma 180 (hereinafter, S-180A for brevity) and a group of six mice was used for each compound.

NOTE 2

T/C (%) is an index showing the decrease in the volume of cancer cells (S-180A) which were sedimented when each of these compounds (therapeutic agents) was intraperitoneally administered for five consecutive days to pure strain mice (BDF mice), and after a lapse of a certain number of days, the cancer cells were centrifugally separated from the fluid in the peritoneal cavity. The T/C (%) is calculated on the basis of the following relationship.

$$T/C\ (\%) = \frac{\text{Volume of Tumor in Group Treated with Therapeutic Agent}}{\text{Volume of Tumor in Group Not Treated with Therapeutic Agent}} \times 100$$

A lower T/C (%) value is better or it shows that an improvement was attained.

T/C (%) may be graded as follows.

| T/C (%)   | Grade |
|-----------|-------|
| 100 – 66% | –     |
| 65 ≧ 41%  | +     |
| 40 – 11%  | + +   |
| 10 – 0%   | + + + |

The present invention is further illustrated by reference to the following Preparation Example and Examples, but the present invention is not to be construed as being limited to these Examples. Unless otherwise indicated, all percentages, parts, ratios and the like are by weight.

PREPARATION EXAMPLE

Preparation of $N^4$-Hydroxy-2,2'-cyclocytidine

A solution of 15.1 ml of phosphorus oxychloride partially hydrolyzed with 2.96 ml of water was added to a suspension of 4 g of $N^4$-hydroxycytidine (which can be produced as disclosed in N. K. Kochetokov et al., Tetrahedron Letter, 3253 (1967) and N. K. Kochetokov et al., Progr. Nucl. Acid Res. Mol. Biol., Vol. 9, 403 (1969)) in 24 ml of ethyl acetate and refluxed for 2 hours. The resulting solution was concentrated and the residue was dissolved in ice-water. The solution was passed through a column filled with 230 ml of Diaion SK-1B ($H^+$ form, a tradename for an ion exchange resin made by Mitsubishi Chemical Industries, Ltd., Japan). After washing the resin with water, the resin was eluted with a 0.5 N pyridine-formic acid buffer solution (pH 4.5), and the desired fraction was concentrated and evaporated to dryness. The resulting residue was dissolved in water, and the resulting aqueous solution was passed through a column filled with 200 ml of Diaion SA-11B ($Cl^-$ form, a tradename for an ion exchange resin made by Mitsubishi Chemical Industries, Ltd., Japan), and a fraction eluted by water was concentrated, whereby 1.15 g of $N^4$-hydroxy-2,2'-cyclocytidine hydrochloride was obtained. Melting point (decomposition point): 184° C. The thus-obtained compound had the following properties:

Ultraviolet Absorption:
$\lambda_{max}^{H_2O}$ 253 nm
$\lambda_{max}^{H+}$ 242; 273 nm Paper Chromatographic Analysis (solvent system:n-butanol:acetic acid:water = 5:1:2): $R_f$ value 0.34.

Elemental analysis showed that the found value agreed with the calculated value as shown below:

Elemental Analysis for $C_9H_{12}N_3O_5Cl$: Calcuated (%): C: 38.93: H: 4.36: N: 15.13. Found (%): C: 38.72: H: 4.41: N: 15.08.

EXAMPLE 1

Preparation of $N^4$-Acetoxy-2,2'-cyclocytidine 0.2 g of crystalline $N^4$-hydroxy-2,2'-cyclocytidine (melting point: 218° C., decomp.; UV spectrum $\lambda_{max}^{H_2O}$ 255 nm, $\lambda_{max}^{H+}$ 245, 269 nm) obtained by treating $N^4$-hydroxy-2,2'-cyclocytidine hydrochloride in a conventional manner with an ion exchange resin, Dowex 1 × 2 (bicarbonate form, tradename for an ion exchange resin, produced by Dow Chemical) was dissolved in 2 ml of N,N-dimethylformamide. Acetic anhydride (0.3 ml) was added, and the mixture was stirred at room temperature (about 20°–30° C.) for 5 minutes, after which the reaction was performed at 4° C. for 3 hours with stirring. To the reaction mixture was added 2 ml of ethanol, and the mixture was allowed to stand overnight at room temperature. The solvent was distilled off under reduced pressure, and the residue was crystallized from ethanol to obtain 215 mg (yield: 91.5%) of $N^4$-acetoxy-2,2'-cyclocytidine.

Melting Point: 193°–197° C.

Ultraviolet Absorption Spectrum:
$\lambda_{max}^{pH\ 7}$ ($\epsilon \times 10^{-3}$) 256 nm (19.7)
$\lambda_{max}^{pH\ 2}$ 240 (9.6), 272 nm (12.0)
$\lambda_{max}^{pH\ 12}$ 258 nm (18.0)

NMR Spectrum ($\delta$):
7.50, 7.39 (d.d, 1H, $C_6$ - H)
6.20 (d, 1H, $C_{1'}$ - H),
5.90, 5.84 (d.d, 1H, $C_5$ - H)
5.17 (d, 1H, $C_{2'}$ - H), 2.03 (s, 3H, acetyl)

Elemental Analysis for $C_{11}H_{13}N_3O_6$: Calculated (%): C: 46.64: H: 4.62: N: 14.83. Found (%): C: 46.60: H: 4.60: N: 14.73.

EXAMPLE 2

Preparation of $N^4$-O-Propionyl-2,2'-cyclocytidine 0.2 g (0.83 millimol) of $N^4$-hydroxy-2,2'-cyclocytidine was dissolved with heating (60° C.) in 2 ml of N,N-dimethylformamide, and under ice cooling, 0.33 g (2.5 millimols) of n-propionic anhydride was added. The mixture was stirred for 3 hours, and then allowed to stand at room temperature for 10 minutes. Ethanol (2 ml) was added to the reaction mixture, and the mixture was allowed to stand overnight at room temperature. The solvent was distilled off under reduced pressure, and the residue was crystallized from ethanol to obtain 0.19 g (yield: 77.1%) of $N^4$-O-propionyl-2,2'-cyclocytidine.

Melting Point: 205°–207° C.

UV Absorption Spectrum:
$\lambda_{max}^{pH\ 7}$ ($\epsilon \times 10^{-3}$) 255 nm (21.2)
$\lambda_{max}^{pH\ 2}$ 240 (9.5), 272 nm (12.7)
$\lambda_{max}^{pH\ 12}$ 257 nm (18.0)

Elemental Analysis for $C_{12}H_{15}N_3O_6$: Calculated (%): C: 46.64: H: 4.62: N: 14.83. Found (%): C: 46.60: H: 4.60: N: 14.73.

EXAMPLE 3

Preparation of $N^4$-O-Butyryl-2,2'-cyclocytidine

Using the procedure set forth in Example 2, 0.22 g (yield: 85.7%) of $N^4$-O-butyryl-2,2'-cyclocytidine was obtained from 0.2 g (0.83 millimol) of $N^4$-hydroxy-2,2'- cyclocytidine, 2 ml of N,N-dimethylformamide, and 0.395 g (2.5 millimols) of n-butyric anhydride.

Melting Point: 183°–185° C.
UV Absorption Spectrum:
$\lambda_{max}^{pH\ 7}$ ($\epsilon \times 10^{-3}$) 256.5 nm (20.3)
$\lambda_{max}^{pH\ 2}$ 240 (10.2), 272 nm (13.0)
$\lambda_{max}^{pH\ 12}$ 258 nm (18.3)
Elemental Analysis for $C_{13}H_{17}N_3O_6$: Calculated (%): C: 50.16; H: 5.51; N: 13.50. Found (%): C: 50.14; H: 5.54; N: 13.42.

EXAMPLE 4

Preparation of $N^4$-O-Hexanoyl-2,2'-cyclocytidine

Using the procedure set forth in Example 2, 0.16 g (yield: 56.9%) of $N^4$-O-hexanoyl-2,2'-cyclocytidine was prepared from 0.2 g (0.83 millimol) of $N^4$-hydroxy-2,2'-cyclocytidine, 0.54 g (2.5 millimols) of n-hexanoic anhydride and 2 ml of DMF.

Melting Point: 140°–142° C.
UV Absorption Spectrum:
$\lambda_{max}^{pH\ 7}$ ($\epsilon \times 10^{-3}$) 256 nm (21.0)
$\lambda_{max}^{pH\ 2}$ 240 (16.0), 272 nm (13.0)
$\lambda_{max}^{pH\ 12}$ 257 nm (18.7)
Elemental Analysis for $C_{15}H_{21}N_3O_6$: Calculated (%): C: 53.10; H: 6.24; N: 12.38. Found (%): C: 53.41; H: 6.30; N: 12.26.

EXAMPLE 5

Preparation of $N^4$-O-Lauroyl-2,2'-cyclocytidine 0.2 g (0.83 millimol) of $N^4$-hydroxy-2,2'-cyclocytidine was dissolved in 4 ml of N,N-dimethylformamide, and then 0.96 g (2.5 millimols) of lauric anhydride was added. The mixture was stirred at 60° C. for 3 hours. To the reaction mixture was added 2.5 ml of ethanol, and the mixture was allowed to stand overnight at room temperature. The solvent was distilled off under reduced pressure, and 20 ml of diethyl ether was added to the residue to wash the residue. The ether-insoluble matter was collected by filtration, and then crystallized from ethanol to obtain 0.26 g (yield: 74.0%) of $N^4$-O-lauroyl-2,2'-cyclocytidine.

Melting Point: 154°–156° C.
UV Absorption Spectrum:
$\lambda_{max}^{pH\ 7}$ ($\epsilon \times 10^{-3}$) 256 nm (20.5)
$\lambda_{max}^{pH\ 2}$ 240 (10.2), 272 nm (13.0)
$\lambda_{max}^{pH\ 12}$ 257 nm (17.0)
Elemental Analysis for $C_{21}H_{33}N_3O_6$: Calculated (%): C: 59.56; H: 7.85; N: 9.92. Found (%): C: 59.85; H: 7.76; N: 9.97.

EXAMPLE 6

Preparation of $N^4$-O-Myristoyl-2,2'-cyclocytidine 0.2 g (0.83 millimol) of $N^4$-hydroxy-2,2'-cyclocytidine was dissolved in 2 ml of water, and then 6 ml of dioxane was added. Then, 0.88 g (2 millimols) of myristic anhydride was added and dissolved therein. The mixture was stirred at 80° C. for 4 hours. The reaction mixture was distilled under reduced pressure. To the residue was added 20 ml of diethyl ether, and the mixture was allowed to stand at room temperature for 2 hours. The ether-insoluble matter was collected by filtration, and recyrstallized from ethanol to obtain 0.33 g (yield: 88.8%) of $N^4$-O-myristoyl-2,2'-cyclocytidine.

Melting Point: 153°–155° C.
UV Absorption Spectrum:
$\lambda_{max}^{pH\ 7}$ ($\epsilon \times 10^{-3}$) 256.5 nm (20.5)
$\lambda_{max}^{pH\ 2}$ 240 (9.8), 272 nm (13.0)
$\lambda_{max}^{pH\ 12}$ 258.5 nm (16.5)
Elemental Analysis for $C_{23}H_{37}N_3O_6$: Calculated (%): C: 61.18; H: 8.26; N: 9.30. Found (%): C: 61.84; H: 8.21; N: 9.07.

EXAMPLE 7

Preparation of $N^4$-O-Palmitoyl-2,2'-cyclocytidine 0.14 g of N,N'-carbonyldiimidazole was added to a solution of 0.25 g of palmitic acid in 6.5 ml of dioxane, and they were reacted at $-10°$ C. for 4 hours. Separately, 0.2 g of $N^4$-hydroxy-2,2'-cyclocytidine was dissolved in DMF, and while cooling the solution at $-10°$ C., the above reaction mixture was added thereto. The resultant mixture was stirred at 0° C. for 1 hour, and then the reaction was performed for another 2 hours at 50° C. The reaction mixture was concentrated under reduced pressure. To the residue was added 20 ml of diethyl ether to wash the residue, and the insoluble matter was crystallized from ethanol to afford 0.35 g (yield: 87.5%) of $N^4$-O-palmitoyl-2,2'-cyclocytidine.

Melting Point: 150°–152° C.
UV Absorption Spectrum:
$\lambda_{max}^{pH\ 7}$ ($\epsilon \times 10^{-3}$) 256 nm (20.0)
$\lambda_{max}^{pH\ 2}$ 240 (9.4), 272 nm (12.0)
$\lambda_{max}^{pH\ 2}$ 258 nm (16.0)
Elemental Analysis for $C_{25}H_{41}N_3O_6$: Calculated (%): C: 62.61; H: 8.62; N: 8.76. Found (%): C: 62.45; H: 8.64; N: 8.68.

EXAMPLE 8

Preparation of $N^4$-O-Stearoyl-2,2'-cyclocytidine:

0.2 g (0.83 millimol) of $N^4$-hydroxy-2,2'-cyclocytidine was dissolved in 2 ml of water, and then 6 ml of dioxane and 1.1 g (2 millimols) of stearic anhydride were added thereto and dissolved therein. The mixture was stirred at 80° C. for 4 hours. The reaction mixture was distilled under reduced pressure. To the residue was added 20 ml of diethyl ether, and the mixture was allowed to stand at room temperature for 2 hours. The ether-insoluble matter was collected by filtration, and crystallized from ethanol to afford 0.35 g (yield: 83.1%) of $N^4$-O-stearoyl-2,2'-cyclocytidine.

Melting Point: 144°–148° C.
UV Absorption Spectrum:
$\lambda_{max}^{pH\ 7}$ ($\epsilon \times 10^{-3}$) 256 nm (21.0)
$\lambda_{max}^{pH\ 2}$ 239 (9.9), 272 nm (12.7)
$\lambda_{max}^{pH\ 12}$ 257 nm (17.8)
Elemental Analysis for $C_{27}H_{45}N_3O_6$: Calculated (%): C: 63.88; H: 8.93; N: 8.28. Found (%): C: 63.68; H: 8.95; N: 7.95.

Using the same procedure as above, the following $N^4$-acyloxy-2,2'-cyclocytidines were prepared using the corresponding carboxylic acids or anhydrides thereof.

$N^4$-O-Valeryl-2,2'-cyclocytidine

Yield: 60.0%; melting point: 169°–171° C.; elemental analysis for $C_{14}H_{19}N_3O_6$: found(%) (calculated(%)) C: 51.48 (51.69), H: 5.79 (5.89), N: 13.16 (12.92); maximum UV absorption ($\epsilon \times 10^{-3}$) pH 7: 256 nm (22.0), pH 2: 240 (10.2), 272 nm (13.0), pH 12: 257.5 nm (18.8).

$N^4$-O-Heptanoyl-2,2'-cyclocytidine

Yield: 67.9%; melting point: 164°–165.5° C.; elemental analysis for $C_{16}H_{23}N_3O_6$: found(%) (calculated(%)) C: 54.57 (54.38), H: 6.67 (6.56), N: 11.70 (11.89); maximum UV absorption ($\epsilon \times 10^{-3}$) pH 7: 256 nm (21.0), pH 2: 240 (9.7), 272 nm (12.7), pH 12: 257 nm (18.0).

N$^4$-O-Octanoyl-2,2'-cyclocytidine

Yield: 65.3%; melting point: 161°–163° C.; elemental analysis values for C$_{17}$H$_{25}$N$_3$O$_6$: found(%) (calculated(%)) C: 55.97 (55.58), H: 6.95 (6.86), N: 11.31 (11.44); maximum UV absorption ($\epsilon \times 10^{-3}$) pH 7: 256 nm (21.0), pH 2: 240 (9.7), 272 nm (12.6), pH 12: 257 nm (18.0).

N$^4$-O-Decanoyl-2,2'-cyclocytidine

Yield: 80.8%; melting point 156°–158° C.; elemental analysis values for C$_{19}$H$_{29}$N$_3$O$_6$: found(%) (calculated(%)) C: 57.66 (57.71), H: 7.44 (7.39), N: 10.29 (10.63), maximum UV absorption ($\epsilon \times 10^{-3}$) pH 7: 256 nm (19.8), pH 2: 240 (9.5), 272 nm (16.0), pH 12: 257 nm (16.0).

EXAMPLE 9

Preparation of N$^4$,3',5'-Tri-O-lauroyl-2,2'-cyclocytidine:

To 0.2 g (0.72 millimol) of N$^4$-hydroxy-2,2'-cyclocytidine (hydrochloride) were added 4 ml of N,N-dimethylformamide and 15 ml of pyridine and dissolved therein. To the solution was added 1.38 g (3.6 millimols) of lauric anhydride, and the mixture was stirred at 120° C. for 10 hours. The reaction mixture was concentrated, and 10 ml of a 50% aqueous solution of ethanol was added thereto. The mixture was allowed to stand at room temperature for 3 hours with stirring. The reaction mixture was concentrated under reduced pressure, and diethyl ether was added to the residue. The mixture was allowed to stand overnight in a cold place. The precipitate that formed was collected by filtration, and crystallized from ethanol to obtain 0.79 g (yield: 55.7%) of N$^4$,3',5'-tri-O-lauroyl-2,2'-cyclocytidine.

Melting Point: 155°–158° C.
Maximum UV Absorption:
$\lambda_{max}^{pH\ 7}$ ($\epsilon \times 10^{-3}$) 256 nm (22.0)
$\lambda_{max}^{pH\ 2}$ 240 (s) (10.4), 266 nm (13.6)
$\lambda_{max}^{pH\ 12}$ 257.5 nm (19.5)
Elemental Analysis for C$_{45}$H$_{77}$N$_3$O$_8$: Calculated (%): C: 68.57; H: 9.85; N: 5.32. Found (%): C: 68.58; H: 9.79; N: 5.20.

EXAMPLE 10

Preparation of N$^4$,3',5'-Tri-O-butyryl-2,2'-cyclocytidine:

To 0.2 g (0.72 millimol) of N$^4$-hydroxy-2,2'-cyclocytidine (hydrochloride) were added 15 ml of pyridine and 0.57 g (3.6 millimols) of n-butyric anhydride, and the mixture was stirred at room temperature for 30 hours. The reaction mixture was concentrated, and 10 ml of a 50% aqueous solution of ethanol was added to the residue. The mixture was allowed to stand at room temperature for 3 hours. The reaction mixture was concentrated under reduced pressure, and diethyl ether was added to the residue. The mixture was allowed to stand overnight at 5° C. The precipitate that formed was collected by filtration and crystallized from a small amount (3 ml) of a water-ethanol mixture (1:4 by volume) to obtain 0.14 g (yield: 42.9%) of N$^4$,3',5'-tri-O-butyryl-2,2'-cyclocytidine.

Melting Point: 157°–160° C.
Maximum UV Absorption:
$\lambda_{max}^{pH\ 7}$ ($\epsilon \times 10^{-3}$) 254 nm (18.0)
$\lambda_{max}^{pH\ 2}$ 240 (s) (10.0), 265 nm (13.0)
$\lambda_{max}^{pH\ 12}$ 258 nm (16.0).
Elemental Analysis for C$_{21}$H$_{28}$N$_3$O$_8\cdot\frac{1}{2}$H$_2$O: Calculated (%): C: 54.90; H: 6.57; N: 9.15. Found (%): C: 54.98; H: 6.37; N: 9.17.

EXAMPLE 11

Preparation of N$^4$,3',5'-Tri-O-myristoyl-2,2'-cyclocytidine:

Using 0.2 g (0.72 millimol) of N$^4$-hydroxy-2,2'-cyclocytidine hydrochloride and 1.58 g (3.6 millimols) of myristic anhydride, 0.29 g (yield: 40.4%) of N$^4$,3',5'-tri-O-myristoyl-2,2'-cyclocytidine was prepared employing the procedure of Example 9.

Melting Point: 142°–146° C.
Maximum UV Absorption:
$\lambda_{max}^{pH\ 7}$ ($\epsilon \times 10^{-3}$) 236 (9.9), 265 nm (11.0)
$\lambda_{max}^{pH\ 2}$ 236 (9.6), 265 nm (11.0)
$\lambda_{max}^{pH\ 12}$ 277 nm (9.5)
Elemental Analysis for C$_{51}$H$_{89}$N$_3$O$_8\cdot$2H$_2$O: Calculated (%): C: 67.43; H: 10.09; N: 4.63. Found (%): C: 67.06; H: 10.05; N: 4.78.

Using quite the same procedure as set forth above, the following N$^4$,3',5'-tri-O-acyl-2,2'-cyclocytidines were prepared from the corresponding fatty acid anhydrides.

N$^4$,3',5'-Tri-O-acetyl-2,2'-cyclocytidine

Yield: 68.2%
Melting Point: 178°–182° C.
UV Absorption Maximum:
$\lambda_{max}^{pH\ 7}$ ($\epsilon \times 10^{-3}$) 253 nm (16.0)
$\lambda_{max}^{pH\ 2}$ 240 (9.0) 272 nm (10.9)
$\lambda_{max}^{pH\ 12}$ 258 nm (15.3)
Elemental Analysis for C$_{15}$H$_{17}$N$_3$O$_8$: Calculated (%): C: 49.05; H: 4.67; N: 11.44. Found (%): C: 49.26; H: 4.65; N: 11.36.

N$^4$,3',5'-Tri-O-propionyl-2,2'-cyclocytidine

Yield: 58.5%
Melting Point: 140°–142° C.
UV Absorption Maximum:
$\lambda_{max}^{pH\ 7}$ ($\epsilon \times 10^{-3}$) 256 nm (18.6)
$\lambda_{max}^{pH\ 2}$ 240 (s) (9.9) 265 nm (12.7)
$\lambda_{max}^{pH\ 12}$ 258.5 nm (17.0)
Elemental Analysis for C$_{18}$H$_{23}$N$_3$O$_8\cdot\frac{1}{2}$H$_2$O: Calculated (%): C: 51.67; H: 5.78; N: 10.04. Found (%): C: 51.67; H: 5.51; N: 10.30.

N$^4$,3',5'-Tri-O-valeryl-2,2'-cyclocytidine

Yield: 68.4%
Melting Point: 168°–170° C.
UV Absorption Maximum:
$\lambda_{max}^{pH\ 7}$ ($\epsilon \times 10^{-3}$) 253 nm (16.5)
$\lambda_{max}^{pH\ 2}$ 240 (s) (10.3) 264 nm (14.0)
$\lambda_{max}^{pH\ 12}$ 258.5 nm (15.3)
Elemental Analysis for C$_{24}$H$_{35}$N$_3$O$_8\cdot\frac{1}{4}$H$_2$O: Calculated (%): C: 57.88; H: 7.18; N: 8.44. Found (%): C: 57.88; H: 6.98; N: 8.43.

N$^4$,3',5'-Tri-O-hexanoyl-2,2'-cyclocytidine

Yield: 52.6%
Melting Point: 189°–192° C.
UV Absorption Maximum:
$\lambda_{max}^{pH\ 7}$ ($\epsilon \times 10^{-3}$) 252.5 nm (15.7)
$\lambda_{max}^{pH\ 2}$ 240 (s) (10.0) 267 nm (12.4)
$\lambda_{max}^{pH\ 12}$ 258 nm (15.0)

Elemental Analysis for $C_{27}H_{41}N_3O_8$: Calculated (%): C: 60.77; H: 7.37; N: 7.87. Found (%): C: 60.61; H: 7.76; N: 7.83.

$N^4,3',5'$-Tri-O-heptanoyl-2,2'-cyclocytidine

Yield: 64.3%
Melting Point: 160°–164° C.
UV Absorption Maximum:
$\lambda_{max}^{pH\ 7}$ ($\epsilon \times 10^{-3}$) 255.5 nm (20.0)
$\lambda_{max}^{pH\ 2}$ 240 (9.9) 268 nm (13.0)
$\lambda_{max}^{pH\ 12}$ 258 nm (17.0)
Elemental Analysis for $C_{30}H_{47}N_3O_8 \cdot \frac{1}{2}H_2O$: Calculated (%): C: 61.40; H: 8.24; N: 7.16. Found (%): C: 61.29; H: 8.22; N: 7.06.

$N^4,3',5'$-Tri-O-octanoyl-2,2'-cyclocytidine

Yield: 39.5%
Melting Point: 187°–189° C.
UV Absorption Maximum:
$\lambda_{max}^{pH\ 7}$ ($\epsilon \times 10^{-3}$) 252 nm (15.3)
$\lambda_{max}^{pH\ 2}$ 240 (s) (9.7) 267 nm (12.0)
$\lambda_{max}^{pH\ 12}$ 258 nm (16.4)
Elemental Analysis for $C_{33}H_{53}N_3O_8$: Calculated (%): C: 63.74; H: 8.92; N: 6.76. Found (%): C: 63.67; H: 8.66; N: 6.66.

$N^4,3',5'$-Tri-O-decanoyl-2,2'-cyclocytidine

Yield: 51.1%
Melting Point: 167°–169° C.
UV Absorption Maximum:
$\lambda_{max}^{pH\ 7}$ ($\epsilon \times 10^{-3}$) 253 nm (16.7)
$\lambda_{max}^{pH\ 2}$ 240 (s) (10.5) 266 nm (13.5)
$\lambda_{max}^{pH\ 12}$ 257.5 nm (17.0)
Elemental Analysis for $C_{39}H_{65}N_3O_8$: Calculated (%): C: 66.54; H: 9.31; N: 5.97. Found (%): C: 66.69; H: 9.41; N: 5.83.

$N^4,3',5'$-Tri-O-palmitoyl-2,2'-cyclocytidine

Yield: 42.3%
Melting Point: 145°–149° C.
UV Absorption Maximum:
$\lambda_{max}^{pH\ 7}$ ($\epsilon \times 10^{-3}$) 226 (18.5) 255 nm (15.9)
$\lambda_{max}^{pH\ 2}$ 227 (21.7) 267 nm (10.8)
$\lambda_{max}^{pH\ 12}$ 256 nm (16.2)
Elemental Analysis for $C_{57}H_{101}N_3O_8$: Calculated (%): C: 71.58; H: 10.64; N: 4.39. Found (%): C: 71.49; H: 10.79; N: 4.43.

$N^4,3',5'$-Tri-O-stearoyl-2,2'-cyclocytidine

Yield: 35.4%
Melting Point: 144°–150° C.
UV Absorption Maximum:
$\lambda_{max}^{pH\ 7}$ ($\epsilon \times 10^{-3}$) 225 (19.0) 255 nm (16.0)
$\lambda_{max}^{pH\ 2}$ 225 (22.0) 270 nm (11.0)
$\lambda_{max}^{pH\ 12}$ 255 nm (16.0)

Elemental Analysis for $C_{63}H_{113}N_3O_8 \cdot \frac{1}{2}H_2O$: Calculated (%): C: 72.51; H: 10.43; N: 4.03. Found (%): C: 72.62; H: 10.77; N: 4.30.

While the invention has been described in detail and with reference to specific embodiments thereof, it will be apparent to one skilled in the art that various changes and modifications can be made therein without departing from the spirit and scope thereof.

What is claimed is:

1. A compound selected from the group consisting of $N^4$-Acyloxy-2,2'-cyclocytidine compounds and $N^4,3',5'$-tri-O-acyl-2,2'-cyclocytidine compounds of the formula

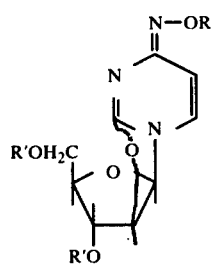

(I)

wherein the two R' moieties are both a hydrogen atom, or are the same as R which represents an acyl group derived from a fatty acid containing 1 to 46 carbon atoms or a cyclic carboxylic acid containing 5 to 11 carbon atoms, in which the ring may be substituted with one or more of a chlorine atom, a methyl group, a methoxy group or a nitro group; and the pharmaceutically acceptable salts thereof.

2. The compounds and the pharmaceutically acceptable salts thereof as set forth in claim 1, wherein the two R' moieties are both a hydrogen atom, or are the same as R which represents an acyl group derived from a fatty acid containing 1 to 20 carbon atoms or a cyclic carboxylic acid containing 5 to 11 carbon atoms, in which the ring may be substituted with one or more of a chlorine atom, a methyl group, a methoxy group or a nitro group.

3. The compounds and the pharmaceutically acceptable salts thereof as set forth in claim 1, wherein the two R' moieties are both a hydrogen atom, or are the same as R which represents an acetyl, propionyl, butyryl, valeryl, hexanoyl, heptanoyl, octanoyl, decanoyl, lauroyl, myristoyl, palmitoyl, stearoyl, benzoyl, p-chlorobenzoyl, p-nitrobenzoyl, phenylacetyl, p-toluyl, o-toluyl, 3,4,5-trimethoxybenzoyl, 1-adamantanecarbonyl, 5-norbornene-2-carbonyl or cyclobutanecarbonyl group.

4. The compounds and the pharmaceutically acceptable salts thereof as set forth in claim 1, wherein the two R' moieties are both a hydrogen atom, or are the same as R which represents an acetyl, propionyl, butyryl, valeryl, hexanoyl, heptanoyl, octanoyl, decanoyl, lauroyl, myristoyl, palmitoyl or stearoyl group.

* * * * *